(12) United States Patent
Scirica et al.

(10) Patent No.: US 7,172,104 B2
(45) Date of Patent: Feb. 6, 2007

(54) SURGICAL STAPLING APPARATUS

(75) Inventors: Paul A. Scirica, Huntington, CT (US); Roman Czernik, Trumbull, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 130 days.

(21) Appl. No.: 11/059,804

(22) Filed: Feb. 17, 2005

(65) Prior Publication Data

US 2005/0279804 A1  Dec. 22, 2005

Related U.S. Application Data

(60) Provisional application No. 60/545,620, filed on Feb. 17, 2004.

(51) Int. Cl.
*A61B 17/68* (2006.01)
(52) U.S. Cl. ............................... 227/175.2; 227/176.1; 227/19; 227/180.1
(58) Field of Classification Search ............ 227/175.2, 227/175.1, 176.1, 181.1, 181.2, 19, 180.1
See application file for complete search history.

(56) References Cited

U.S. PATENT DOCUMENTS

| | | | |
|---|---|---|---|
| 3,079,606 A | 3/1963 | Bobrov et al. | |
| 3,490,675 A | 1/1970 | Green et al. | |
| 3,499,591 A | 3/1970 | Green | |
| 4,244,372 A | 1/1981 | Kapitanov et al. | |
| 4,429,695 A | 2/1984 | Green | |
| 4,520,817 A | 6/1985 | Green | |
| 4,589,413 A | 5/1986 | Malyshev et al. | |
| 4,605,001 A | 8/1986 | Rothfuss et al. | |
| 4,608,981 A | 9/1986 | Rothfuss et al. | |
| 4,610,383 A | 9/1986 | Rothfuss et al. | |
| 4,633,861 A | 1/1987 | Chow et al. | |
| 4,633,874 A | 1/1987 | Chow et al. | |
| 4,672,964 A | 6/1987 | Dee et al. | |
| 4,763,669 A | 8/1988 | Jaeger | |
| 4,863,088 A | 9/1989 | Redmond et al. | |
| 4,880,015 A | 11/1989 | Nierman | |
| 4,892,244 A | 1/1990 | Fox et al. | |
| 4,978,049 A | 12/1990 | Green | |
| 4,991,764 A | 2/1991 | Mericle | |
| 5,040,715 A | 8/1991 | Green et al. | |
| 5,065,929 A | 11/1991 | Schulze et al. | |

(Continued)

FOREIGN PATENT DOCUMENTS

DE   4300307   7/1994

(Continued)

*Primary Examiner*—John Sipos
*Assistant Examiner*—Michelle Lopez

(57) ABSTRACT

The present disclosure provides for a loading unit for use with and/or supportable on a distal end of a surgical stapling apparatus. The loading unit includes a housing portion including a connecting feature, preferably in the form of a pair of axially oriented and diametrically opposed slots formed therein, and a drive assembly slidably supported within the housing portion of the loading unit, the drive assembly including a pair of axially spaced apart radially inwardly extending fingers, wherein when the distal end of a control rod of a surgical stapling apparatus is axially advanced in the direction of and engages the resilient fingers, the distal end of the control rod biases the resilient fingers radially outward into the slots of the housing portion.

16 Claims, 15 Drawing Sheets

U.S. PATENT DOCUMENTS

| | | |
|---|---|---|
| 5,071,052 A | 12/1991 | Rodak et al. |
| 5,074,454 A | 12/1991 | Peters |
| 5,083,695 A | 1/1992 | Foslien et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,152,279 A | 10/1992 | Wilk |
| 5,209,747 A | 5/1993 | Knoepfler |
| RE34,519 E | 1/1994 | Fox et al. |
| 5,275,608 A | 1/1994 | Forman et al. |
| 5,282,826 A | 2/1994 | Quadri |
| 5,307,976 A | 5/1994 | Olson et al. |
| 5,312,023 A | 5/1994 | Green et al. |
| 5,318,221 A | 6/1994 | Green et al. |
| 5,326,013 A | 7/1994 | Green et al. |
| 5,330,502 A | 7/1994 | Hassler et al. |
| 5,332,142 A | 7/1994 | Robinson et al. |
| 5,350,391 A | 9/1994 | Iacovelli |
| 5,354,311 A | 10/1994 | Kambin et al. |
| 5,374,277 A | 12/1994 | Hassler |
| 5,376,095 A | 12/1994 | Ortiz |
| 5,383,888 A | 1/1995 | Zvenyatsky et al. |
| 5,397,046 A | 3/1995 | Savage et al. |
| 5,415,334 A | 5/1995 | Williamson, IV et al. |
| 5,415,335 A | 5/1995 | Knodel, Jr. |
| 5,433,721 A | 7/1995 | Hooven et al. |
| 5,465,895 A | 11/1995 | Knodel et al. |
| 5,467,911 A | 11/1995 | Tsuruta et al. |
| 5,474,566 A | 12/1995 | Alesi et al. |
| 5,474,571 A | 12/1995 | Lang |
| 5,484,451 A | 1/1996 | Akopov et al. |
| 5,486,185 A | 1/1996 | Freitas et al. |
| 5,487,500 A | 1/1996 | Knodel et al. |
| 5,507,426 A | 4/1996 | Young et al. |
| 5,535,935 A | 7/1996 | Vidal et al. |
| 5,582,617 A | 12/1996 | Klieman et al. |
| 5,605,272 A | 2/1997 | Witt et al. |
| 5,630,539 A | 5/1997 | Plyley et al. |
| 5,634,584 A | 6/1997 | Okorocha et al. |
| 5,762,255 A | 6/1998 | Chrisman et al. |
| 5,797,537 A | 8/1998 | Oberlin et al. |
| 5,820,009 A | 10/1998 | Melling et al. |
| 5,901,895 A | 5/1999 | Heaton et al. |
| 6,010,054 A | 1/2000 | Johnson et al. |
| 6,032,849 A | 3/2000 | Mastri et al. |
| 6,241,139 B1 | 6/2001 | Milliman et al. |

FOREIGN PATENT DOCUMENTS

| | | |
|---|---|---|
| EP | 0484677 | 5/1992 |
| EP | 059306 | 3/1994 |
| EP | 0591946 | 4/1994 |
| EP | 0592243 | 4/1994 |
| EP | 0621009 | 10/1994 |
| EP | 0656188 | 6/1995 |
| FR | 2681775 | 10/1991 |

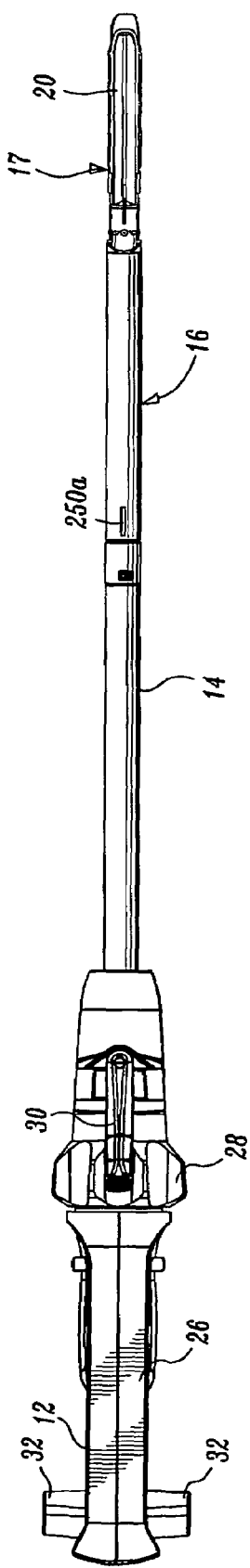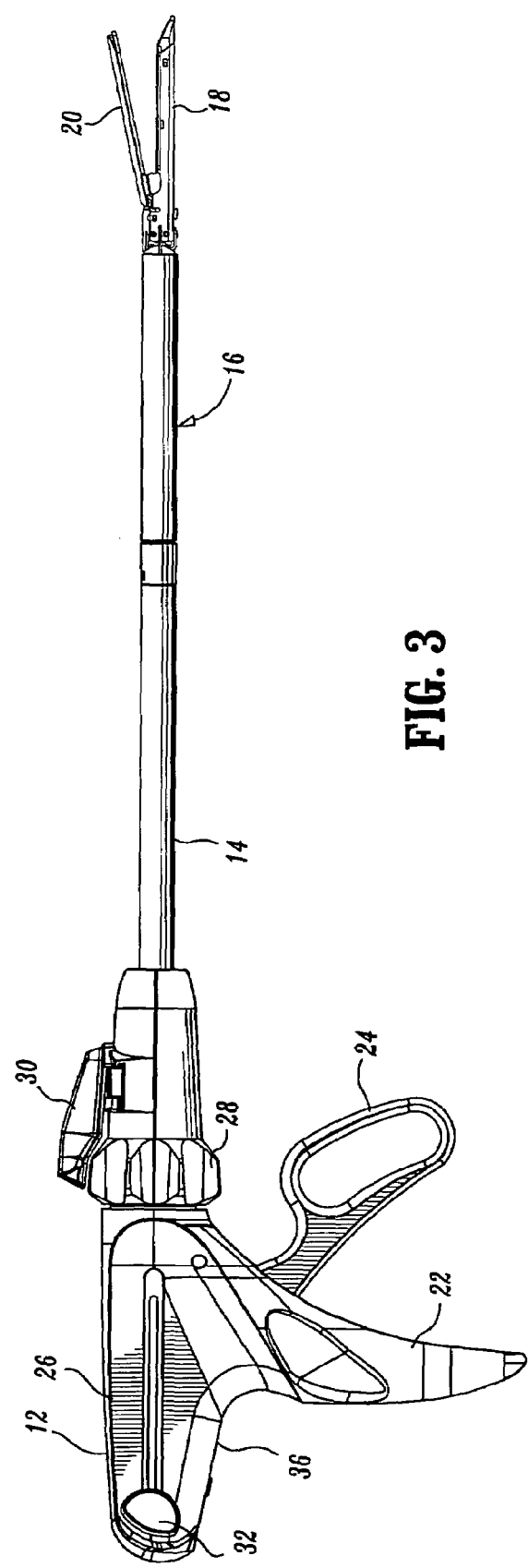
FIG. 2
FIG. 3

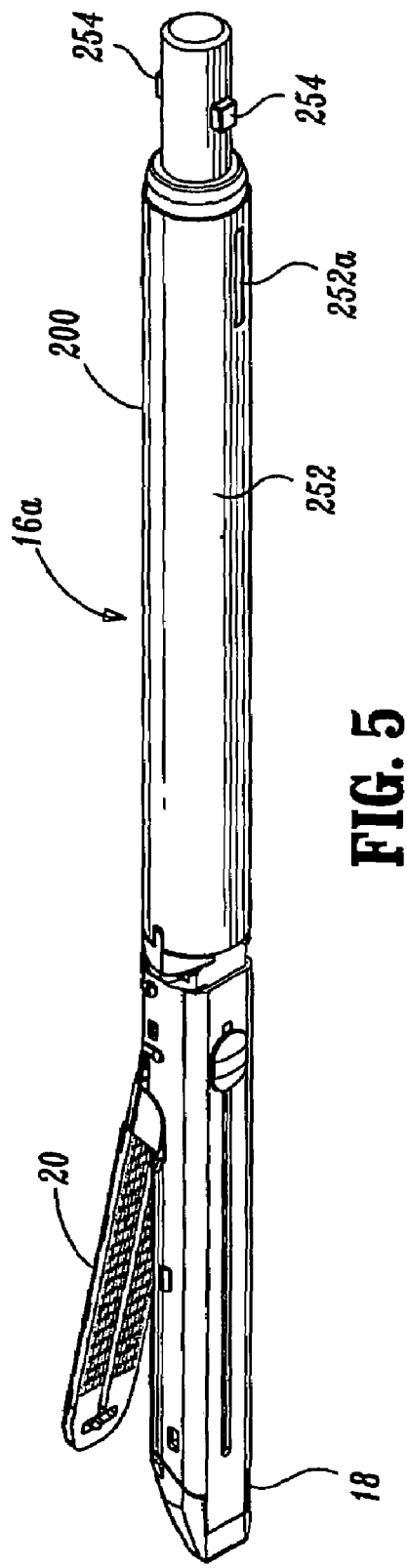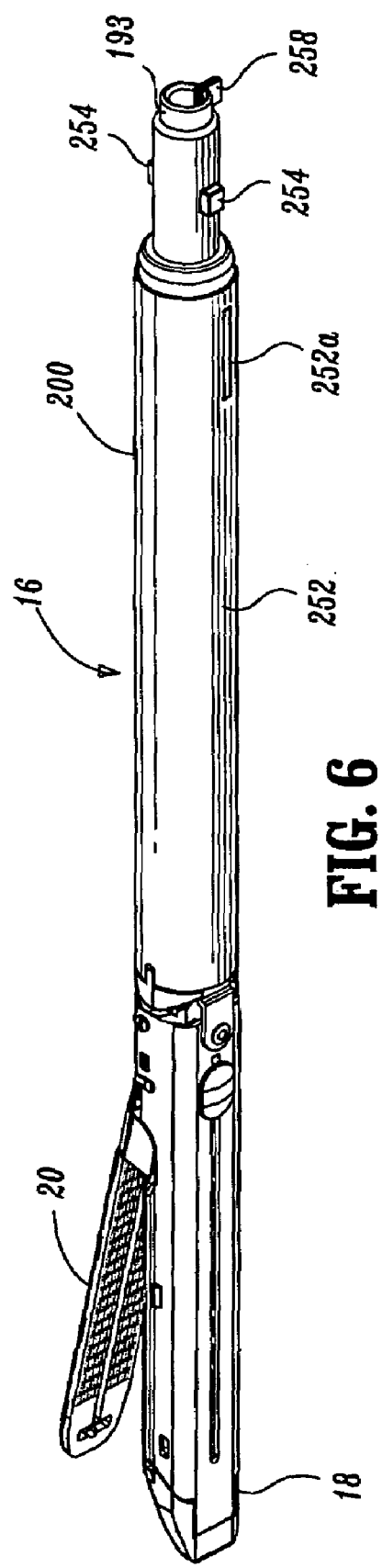

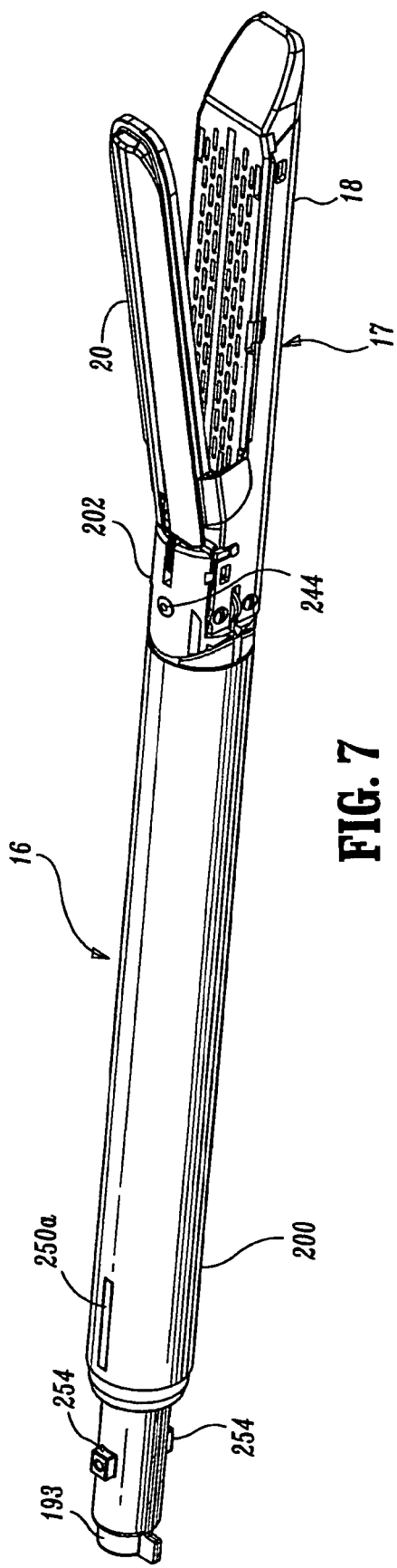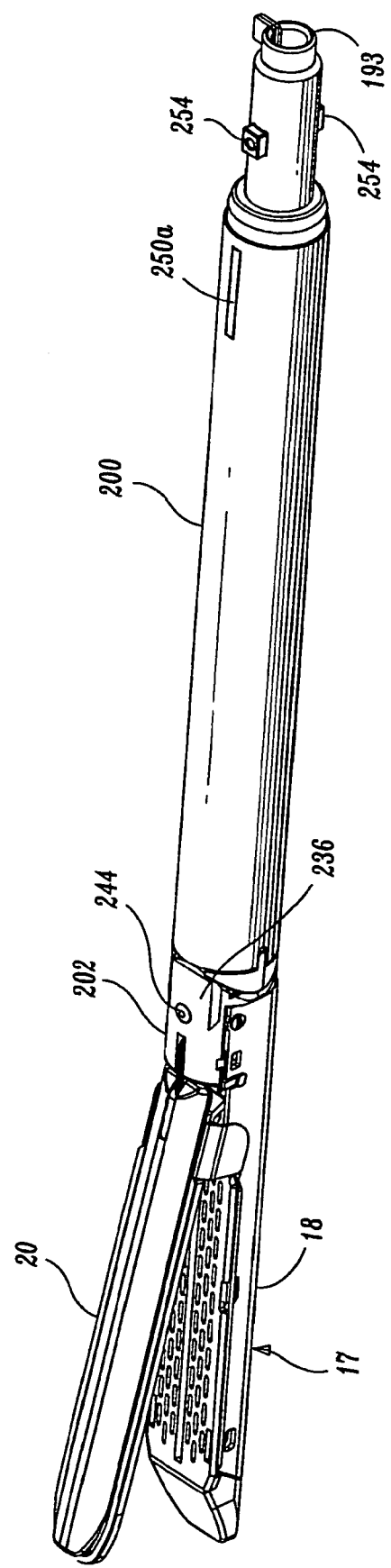

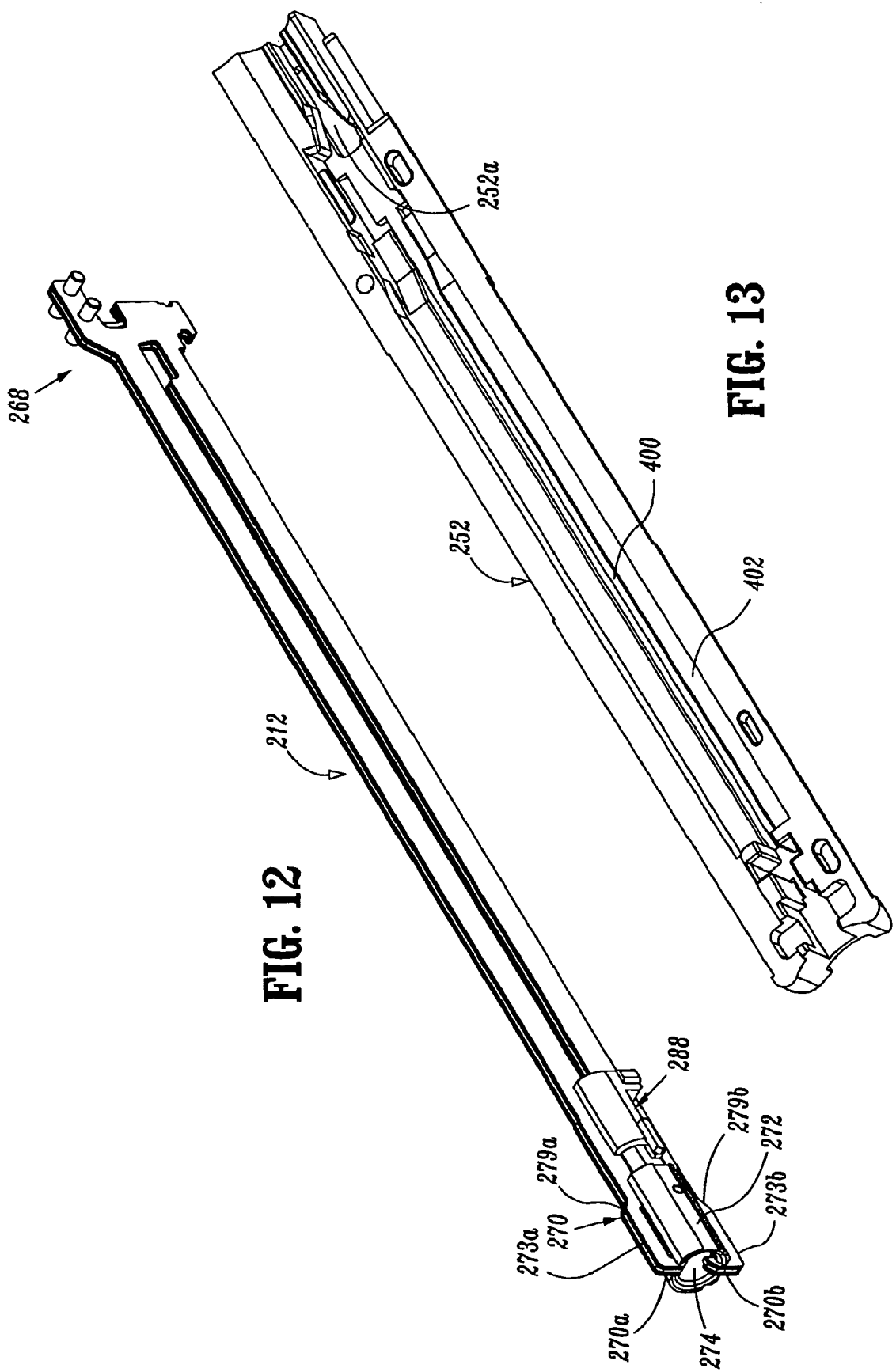

SURGICAL STAPLING APPARATUS

CROSS-REFERENCE TO RELATED APPLICATION

The present application claims the benefit of and priority to U.S. Provisional Application Ser. No. 60/545,620, filed Feb. 17, 2004, the entire content of which being incorporated herein by reference.

BACKGROUND

1. Technical Field

The present disclosure relates to a surgical apparatus, e.g., a surgical stapling apparatus. More particularly, the present disclosure relates to an endoscopic surgical stapling apparatus that includes a connecting feature for connecting the drive assembly of a loading unit, e.g., a single use loading unit ("SULU") or disposable loading unit ("DLU") onto the drive member or control rod of a surgical stapling apparatus, to ensure proper or complete engagement of the SULU or DLU, especially its drive assembly, to the surgical stapling apparatus. For simplicity, hereinafter, SULU or DLU will be referred to as "DLU", but it should be understood to include either or both a DLU or SULU.

2. Background of Related Art

Surgical devices wherein tissue is first grasped or clamped between opposing jaw structure and then joined by surgical fasteners are well known in the art. In some instruments a knife is provided to cut the tissue which has been joined by the fasteners. The fasteners are typically in the form of surgical staples but two part polymeric fasteners can also be utilized.

Instruments for this purpose can include two elongated jaw members which are respectively used to capture or clamp tissue. Typically, one of the jaw members carries a staple cartridge which houses a plurality of staples arranged in at least two lateral rows while the other jaw member has an anvil that defines a surface for forming the staple legs as the staples are driven from the staple cartridge. Generally, the stapling operation is effected by cam members that travel longitudinally through the staple cartridge, with the cam members acting upon staple pushers to sequentially eject the staples from the staple cartridge. A knife can travel between the staple rows to longitudinally cut and/or open the stapled tissue between the rows of staples. Such instruments are disclosed, for example, in U.S. Pat. No. 3,079,606 and U.S. Pat. No. 3,490,675.

A later stapler disclosed in U.S. Pat. No. 3,499,591 also applies a double row of staples on each side of the incision. This patent discloses a surgical stapler that has a disposable loading unit in which a cam member moves through an elongate guide path between two sets of staggered staple carrying grooves. Staple drive members are located within the grooves and are positioned in such a manner so as to be contacted by the longitudinally moving cam member to effect ejection of the staples from the staple cartridge of the disposable loading unit. Other examples of such staplers are disclosed in U.S. Pat. Nos. 4,429,695 and 5,065,929.

Each of the instruments described above is designed for use in conventional surgical procedures wherein surgeons have direct manual access to the operative site. However, in endoscopic or laparoscopic procedures, surgery is performed through a small incision or through a narrow cannula inserted through small entrance wounds in the skin. In order to address the specific needs of endoscopic and/or laparoscopic surgical procedures, endoscopic surgical stapling devices have been developed and are disclosed in, for example, U.S. Pat. No. 5,040,715 (Green, et al.); U.S. Pat. No. 5,307,976 (Olson, et al.); U.S. Pat. No. 5,312,023 (Green, et al.); U.S. Pat. No. 5,318,221 (Green, et al.); U.S. Pat. No. 5,326,013 (Green, et al.); U.S. Pat. No. 5,332,142 (Robinson, et al.); and U.S. Pat. No. 6,241,139 (Milliman et al.), the entire contents of each of which are incorporated herein by reference.

Tyco Healthcare Group, LP, the assignee of the present application, has manufactured and marketed endoscopic stapling instruments, such as the Multifire ENDO GIA™ 30 and Multifire ENDO GIA™ 60 instruments, for a number of years. These instruments include a surgical stapling apparatus and a DLU. Typically, the DLU is attached to the apparatus immediately prior to surgery. After use, the DLU can be removed from the apparatus and a new DLU can be fastened to the apparatus to perform additional stapling and/or cutting operations. These instruments have provided significant clinical benefits. Nonetheless, improvements to these instruments are still possible.

It would be desirable to provide an improved DLU for a surgical stapling apparatus and an improved surgical stapling apparatus having the DLU loaded thereon.

It would also be desirable to provide a connecting feature for a DLU to assure proper loading of the DLU to the shaft of a surgical stapling apparatus.

Accordingly, it is an object of this disclosure to meet the aforementioned desires.

It is another object of this disclosure to provide a DLU with a connecting feature that provides a proper operative connection between the drive assembly of a DLU and the drive member of a surgical stapling apparatus.

It is another object of this disclosure to provide the above-mentioned DLU that provides such proper connection for a DLU that is already mounted to the apparatus without such a connection.

It is still another object of this disclosure to provide an improved DLU with a connecting feature that assures that if the DLU is not properly initially loaded to the shaft of the elongate body of a surgical stapling apparatus, in that the drive assembly of the DLU is not initially properly engaged by, coupled to or connected to a drive member of the surgical stapling apparatus, the locking or connecting feature nevertheless will assure proper connection of the drive assembly to the drive member and proper operation of the DLU and the surgical stapling apparatus. As one example, the DLU will undertake a proper connection at least during clamping of cartridge and anvil assemblies, and/or during firing of staples. As another example, after firing, the DLU will allow retraction of the drive assembly and opening of the cartridge assembly and/or anvil assembly.

Yet another object of the disclosure is to provide a DLU that, after firing and retraction, can be disconnected from the surgical stapling apparatus.

Still another object of the present disclosure is to provide the above objects in a roticulating, i.e., roticulable, DLU.

SUMMARY

In accordance with the present disclosure, a surgical apparatus, e.g., a surgical stapling apparatus, including an arrangement for ensuring proper engagement or connection of a disposable loading unit to an end of the surgical apparatus is provided. According to one aspect of the present disclosure, the surgical apparatus includes a housing, a control rod extending distally from the housing and having an enlarged distal end, and a loading unit supportable on a distal end of the elongate body.

The loading unit preferably includes a housing portion that can include an upper housing half portion and a lower housing half portion, wherein the housing half portions, e.g., each of the upper and lower housing half portions, include(s) an axially oriented aperture or slot formed therein or therethrough. The loading unit also preferably includes a drive assembly slidably supported within the housing portion of the loading unit, the drive assembly including at least one radially inwardly extending resilient finger. The fingers are adapted such that when the preferably enlarged distal end of the control rod is axially advanced in the direction of and engages the resilient fingers, the enlarged distal end of the control rod biases the fingers radially outwardly towards and into the slots formed in the upper and lower housing halves. Preferably, the slots are radially oriented.

Preferably, each resilient finger includes a tip. More preferably, the tips of the fingers are oriented towards one another. In operation, the resilient fingers return to an unbiased state when the enlarged distal end of the control rod has passed the tips of the resilient fingers.

Desirably, the surgical apparatus is a surgical stapler.

The present disclosure also provides for a loading unit for use with and/or supportable on a distal end of a surgical stapling apparatus. The loading unit includes a housing portion including a connecting feature, preferably in the form of a pair of axially oriented and diametrically opposed slots formed therein, and a drive assembly slidably supported within the housing portion of the loading unit, the drive assembly including a pair of axially spaced apart radially inwardly extending fingers, wherein when the distal end of the control rod is axially advanced in the direction of and engages the resilient fingers, the distal end of the control rod biases the resilient fingers radially outward into the slots of the housing portion.

Additional advantages will become apparent from the description which follows, taken in conjunction with the accompanying drawings.

BRIEF DESCRIPTION OF THE DRAWINGS

The present disclosure will be further described with reference to the accompanying drawings, wherein like reference numerals refer to like parts in the several views, and wherein:

FIG. 2 is a top view of the surgical stapling apparatus shown in FIG. 1;

FIG. 3 is a side view of the surgical stapling apparatus shown in FIGS. 1 and 2;

FIG. 5 is a bottom perspective view of a non-articulating DLU;

FIG. 6 is a bottom perspective view of the preferred articulating DLU of the surgical stapling apparatus of FIGS. 1–4;

FIG. 7 is a top perspective view of the DLU of FIG. 6;

FIG. 8 is a top perspective view of the DLU of FIGS. 6 and 7;

FIG. 12 is a top perspective view of the axial drive assembly of FIG. 11 of the DLU of FIGS. 6–9;

FIG. 13 is an enlarged top perspective view of the lower housing half of the proximal housing portion of the DLU of FIGS. 6–9;

FIG. 14 is an enlarged perspective view of the distal end of the elongated body of the stapling apparatus shown in FIG. 4;

DETAILED DESCRIPTION OF PREFERRED EMBODIMENTS

Figure 1:
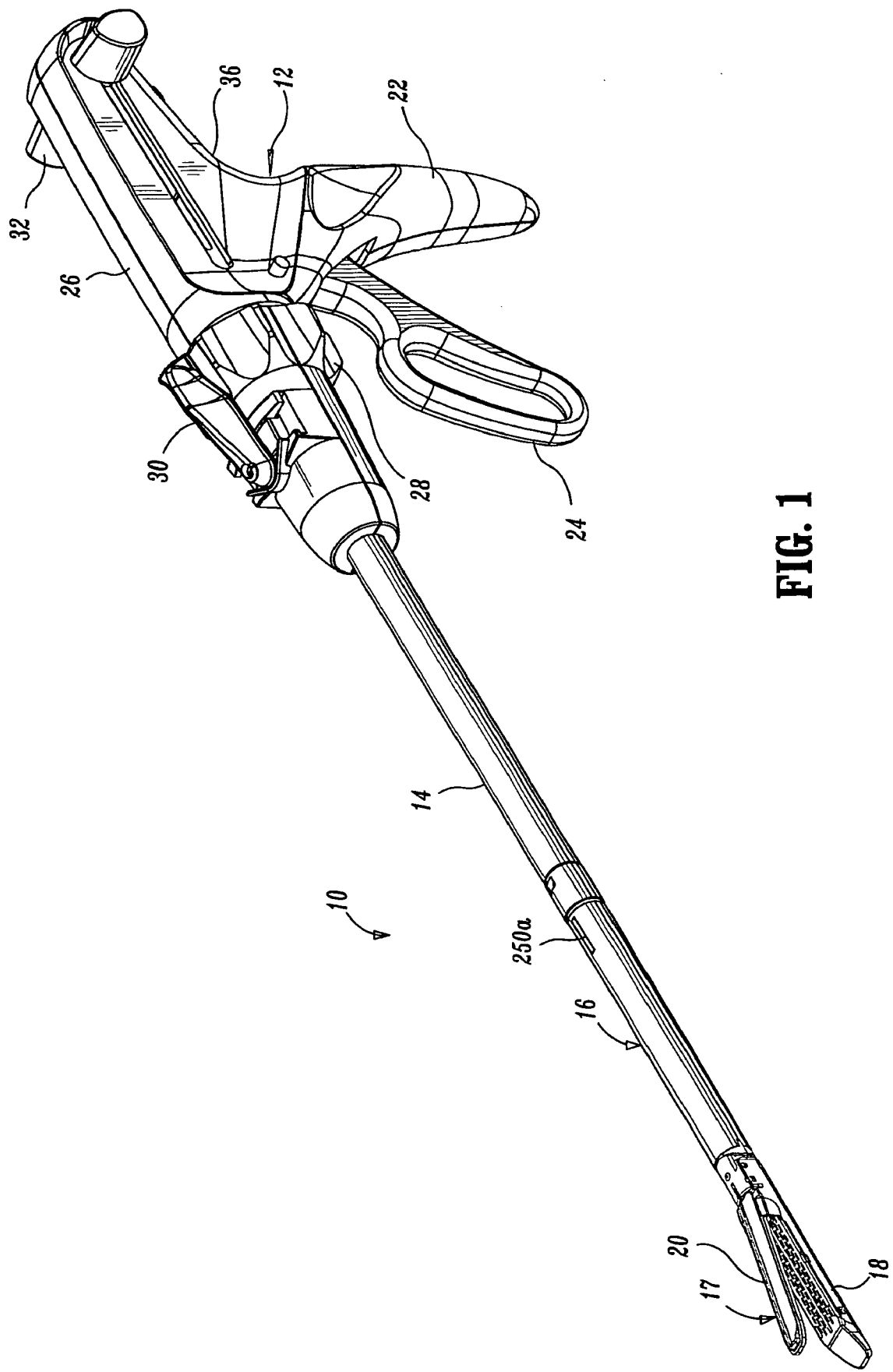
FIG. 1 is a perspective view of a preferred embodiment of the presently disclosed surgical stapling apparatus.

Preferred embodiments of the presently disclosed surgical apparatus, DLU and locking or re-engagement mechanism will now be described in detail with reference to the drawings, in which like reference numerals designate identical or corresponding elements in each of the several views.

In the drawings and in the description that follows, the term "proximal", as is traditional, will refer to the end of the stapling apparatus which is closest to the operator, while the term "distal" will refer to the end of the apparatus which is furthest from the operator.

FIGS. 1–4 show a surgical apparatus, e.g., surgical stapling apparatus, generally referred to as 10. In the interest of brevity, this disclosure will focus primarily on systems, methods and structures for loading, engaging, coupling or connecting a disposable loading unit ("DLU") 16 to surgical stapling apparatus 10. A detailed discussion of the remaining components and method of use of surgical stapling apparatus 10 is disclosed in U.S. Pat. No. 6,241,139.

Surgical stapling apparatus 10 is an endoscopic apparatus and includes a handle assembly 12 and an elongated body 14 extending from handle assembly 12. A DLU 16 is releasably secured to the distal end of elongated body 14. While this disclosure relates to the use of a DLU with surgical stapling apparatus 10, it is understood and within the scope of the present disclosure that a single use loading unit (SULU) or other end effector and/or tool assembly can equally be used in cooperation with surgical stapling apparatus 10.

DLU 16 includes a tool assembly 17 having a cartridge assembly 18 housing a plurality of surgical staples (not shown) and an anvil assembly 20 movably secured in relation to cartridge assembly 18. As shown herein, DLU 16 is configured to apply six (6) linear rows of staples, in DLU's measuring from about 30 mm to about 60 mm in length. DLUs for applying any number of rows of staples, having staple pockets arranged in various patterns and/or DLUs and end effectors having any other lengths, e.g., 45 mm, are also envisioned. Handle assembly 12 includes a stationary handle member 22, a movable handle member 24, and a barrel portion 26.

A rotatable member 28 preferably is mounted on the forward end of barrel portion 26 to facilitate rotation of elongated body 14 and attached DLU 16 with respect to handle assembly 12. An articulation lever 30 preferably is also mounted on the forward end of barrel portion 26 adjacent rotatable member 28 to facilitate articulation of tool assembly 17. Preferably, a pair of knobs 32 are movably positioned along barrel portion 26. Knobs 32 are advanced distally to approximate or close cartridge and/or anvil assembly 18, 20, and retracted proximally to unapproximate or open cartridge and/or anvil assembly 18, 20.

Figure 4:
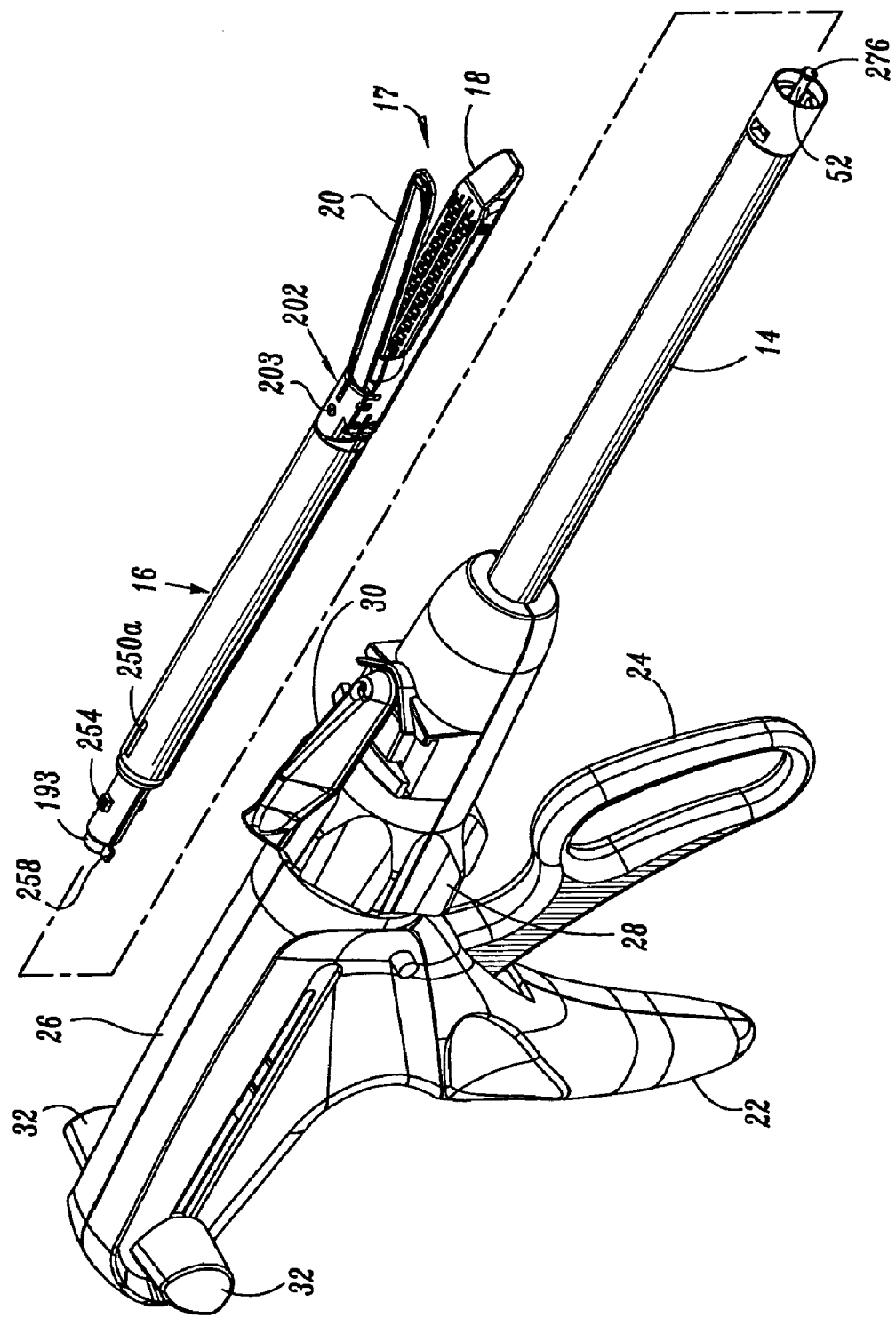
FIG. 4 is a top perspective view of the surgical stapling apparatus of FIGS. 1–3 with the DLU disengaged from the elongate body of the surgical stapling apparatus.

As seen in FIG. 4, DLU 16 is desirably selectively removably couplable to elongated body 14. DLU 16 includes a housing portion 200 having a proximal end adapted to releasably engage the distal end of elongated body 14. A mounting assembly 202 is pivotally secured at 203 to the distal end of housing portion 200, and is configured to receive the proximal end of tool assembly 17 such that pivotal movement of mounting assembly 202 about an axis at 203 perpendicular to the longitudinal axis of housing portion 200 effects articulation of tool assembly 17:

FIGS. 5–8 show various perspective views of DLU 16. Surgical stapling apparatus 10 is capable of receiving a non-articulating DLU 16a, as seen in FIG. 5, or an articulating DLU 16, as seen in FIGS. 6–8. U.S. Pat. No. 6,241,139 includes a detailed discussion of articulating and non-articulating DLU.

With general reference to FIGS. 9–14, 20 and 21 and particular reference to FIGS. 9–14, DLU 16 includes a mounting assembly 235. Mounting assembly 235 includes an upper and a lower mounting portion 236, 238, respectively. A centrally located pivot member 284 extends from each of upper and lower mounting portions 236, 238 through respective openings 246a formed in coupling members 246. Coupling members 246 each include an interlocking proximal portion 246b configured to be received in grooves 290 formed in the proximal end of upper and lower housing halves 250, 252 to retain mounting assembly 235 and upper and lower housing halves 250, 252 in a longitudinally fixed position in relation to each other.

Upper housing half 250 and lower housing half 252 are contained within an outer sleeve, shell or casing 251. The proximal end of upper housing half 250 includes engagement nubs 254 for releasably engaging the distal end of body 14. Nubs 254 form a bayonet-type coupling with the distal end of body 14. Housing halves 252 and 254 define a channel 400 for slidably receiving axial drive assembly 212 therein. An articulation link 256 is dimensioned to be slidably positioned within a slot 402 formed in upper and lower housing halves 250, 252. A pair of blow out plate assemblies 255 are positioned adjacent the distal end of housing portion 200 adjacent the distal end of axial drive assembly 212 to prevent outward buckling and bulging of drive assembly 212 during articulation and firing of surgical stapling apparatus 10. For a detailed discussion of the structure and operation of blow out plate assemblies 255, reference is made to International Application Serial No. PCT/US02/32031, filed on Oct. 4, 2002, entitled "Surgical Stapling Device", the entire content of which is herein incorporated by reference.

Figure 9:
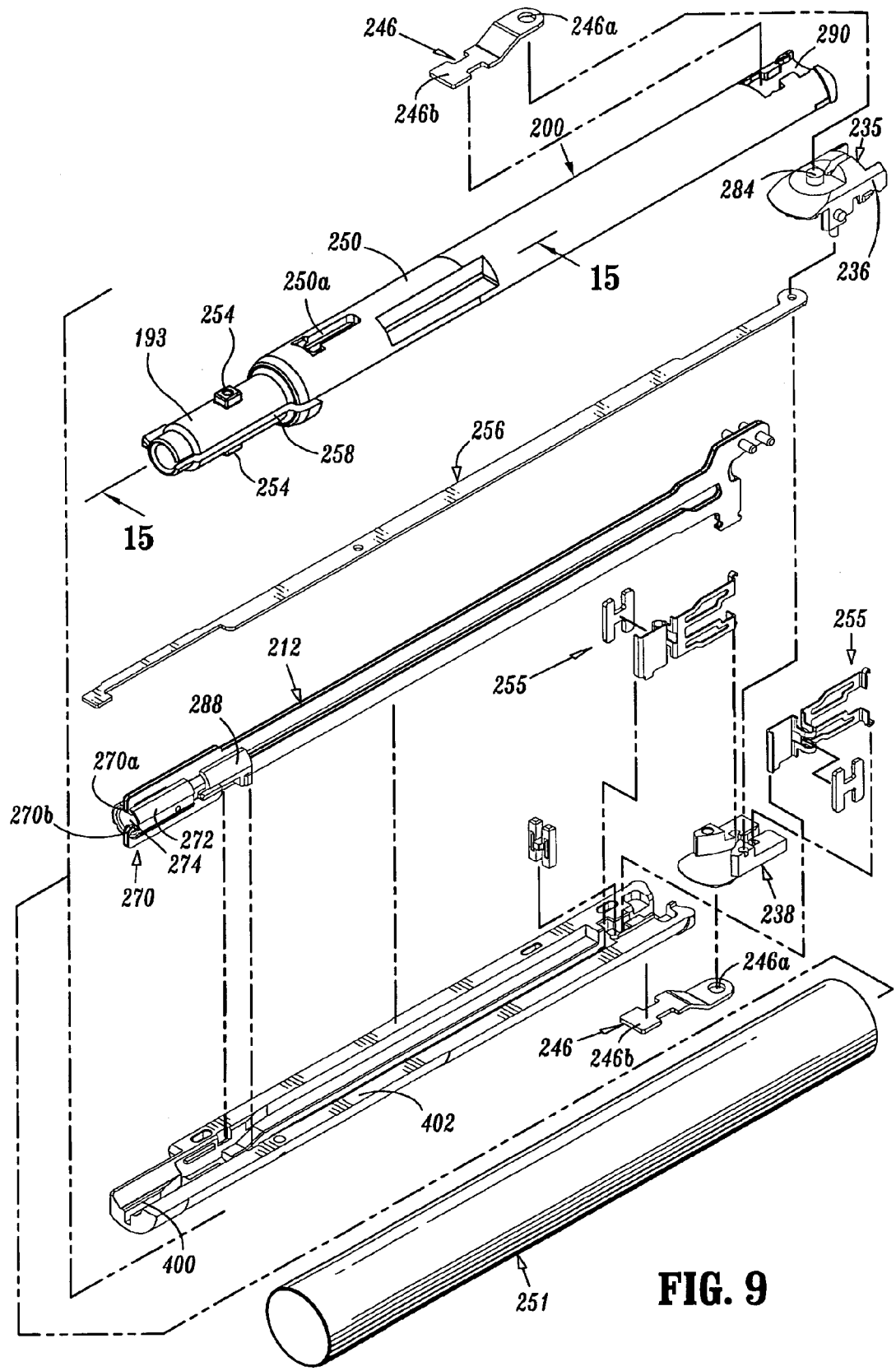
FIG. 9 is an enlarged top perspective view, with parts separated, of the proximal housing portion and mounting assembly of the DLU of FIGS. 6–8.
Figure 10:
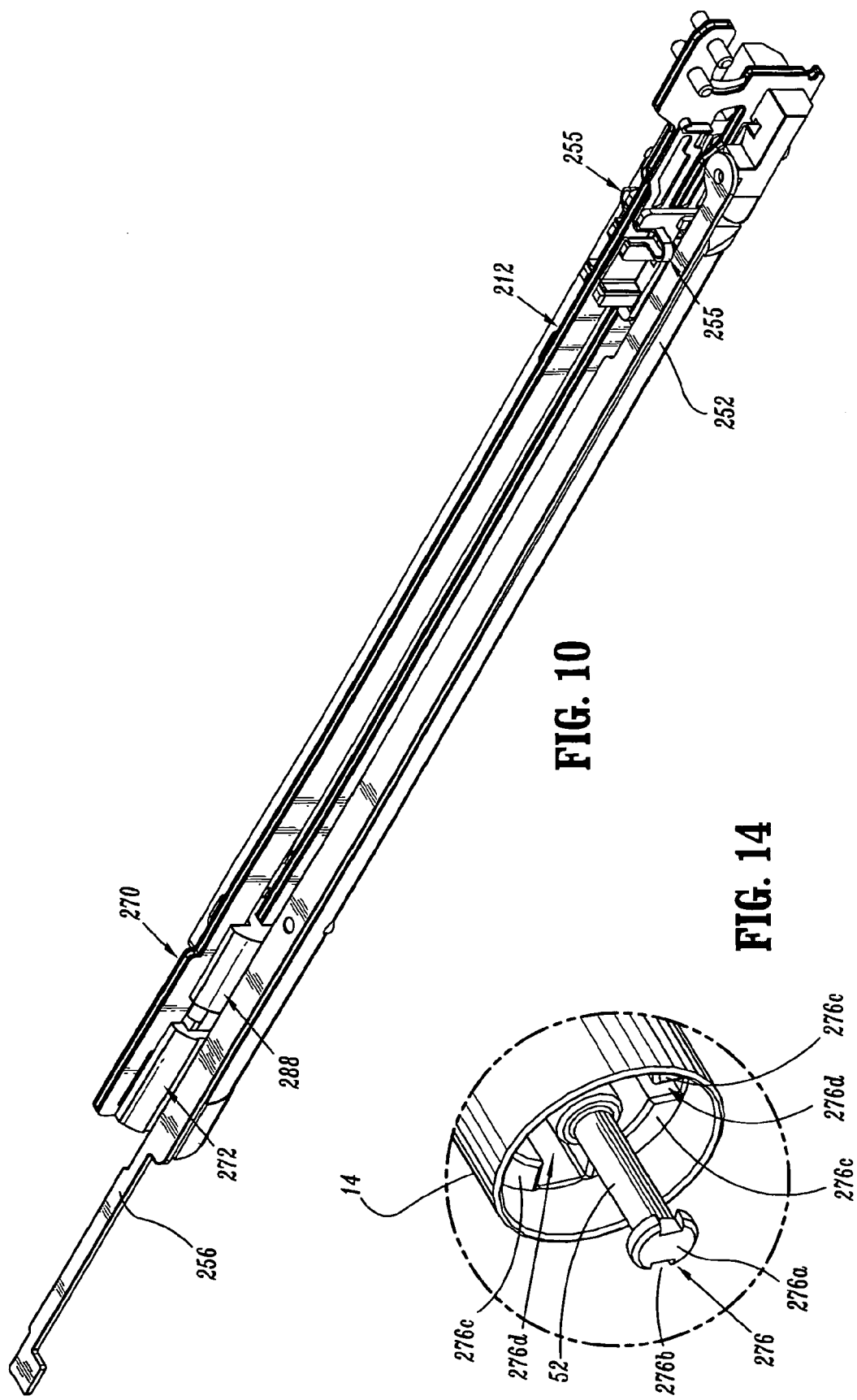
FIG. 10 is a top perspective view of the proximal housing portion and mounting assembly of the DLU of FIGS. 6–9 with the upper housing half removed.

Referring to FIG. 9, optionally, a locking member 288 may be supported on engagement section 270 of axial drive assembly 212. In operation, when axial drive assembly 212 is actuated, by applying a predetermined force to movable handle member 24 to advance axial drive assembly 212 distally, locking member 288 provides an audible and tactile indication that surgical stapling apparatus 10 has been actuated. For a detailed discussion of the structure and operation of locking member 288, reference is made to the aforementioned International Application Serial No. PCT/US02/32031. Locking member 288 may also prevent inadvertent partial actuation of DLU 16, such as during shipping, by locking axial drive assembly 212 at a fixed position within DLU 16 until a predetermined axial force has been applied to axial drive assembly 212.

Figure 11:
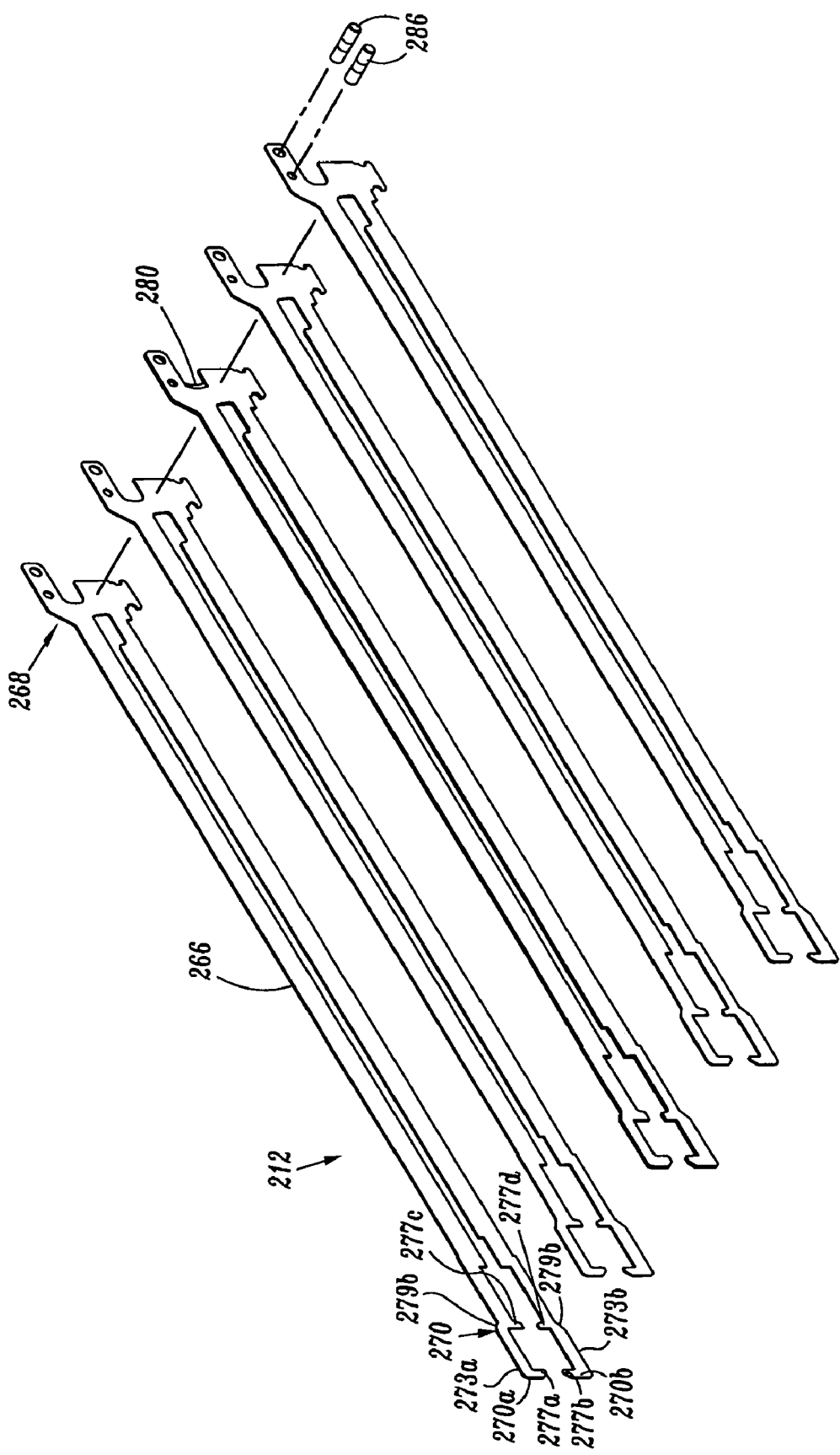
FIG. 11 is a top perspective view, with parts separated, of the axial drive assembly of the DLU of FIGS. 6–9.

With reference to FIGS. 9–12, axial drive assembly 212 includes an elongated drive beam 266 (FIG. 11) including a distal working head 268 (FIG. 12) and a proximal engagement section 270. Drive beam 266 may be constructed from a single sheet of material or, preferably, multiple stacked sheets, as shown in FIG. 11. Engagement section 270 includes a pair of resilient engagement fingers 270a and 270b which are dimensioned and configured to mountingly engage a pair of corresponding retention slots 272a and 272b formed in drive member 272 (FIG. 12). Drive member 272 includes a proximal porthole 274 configured to receive distal end 276 of a drive member, e.g., drive rod or control rod 52 (FIGS. 14 and 16–18) when the proximal end of DLU 16 is being engaged with elongated body 14 of surgical stapling apparatus 10. Control rod 52 functions to impart axial movement of drive assembly 212 from handle assembly 12.

With reference to FIGS. 9–12 and 15–21, each finger 270a, 270b includes a region of increased height, which region preferably is formed of and defines a respective tab 273a, 273b. Each tab 273a, 273b preferably lies in the same plane as the plane defined by drive beam 266.

As seen in FIGS. 1, 4, 7–9 and 15–21, upper housing half 250 includes a longitudinally or axially oriented elongate aperture or slot 250a. Preferably, elongate slot 250a is axially aligned with engagement nub 254 of insertion tip 193. As seen in FIGS. 5, 6, 13 and 15–20, lower housing half 252 includes a longitudinally or axially oriented elongate aperture or slot 252a. Preferably, elongate slot 252a is axially aligned with a respective engagement nub 254 of insertion tip 193 when lower housing half 252 is coupled to upper housing half 250. As will be described in greater detail below, elongate apertures or slots 250a, 252a are sized to allow the upper portions or tabs 273a, 273b of the pair of engagement fingers 270a, 270b of engagement section 270 of axial drive assembly 212 to respectively deflect thereinto during engagement of DLU 16 to the distal end of elongate body 14. While it is preferred that slots 250a, 250b extend completely through upper and lower housing halves 250, 252, it is envisioned that slots 250a, 250b may be in the form of non-through channels, troughs, or grooves formed in the inner surface or through less than the entire thickness of upper and lower housing halves 250, 252. Preferably, the connecting feature of the present invention includes elongate apertures or slots 250a, 252a and tabs 273a, 273b, as well as the operative interengagement of slots 250a, 252a with respective tabs 273a, 273b.

Figure 15:
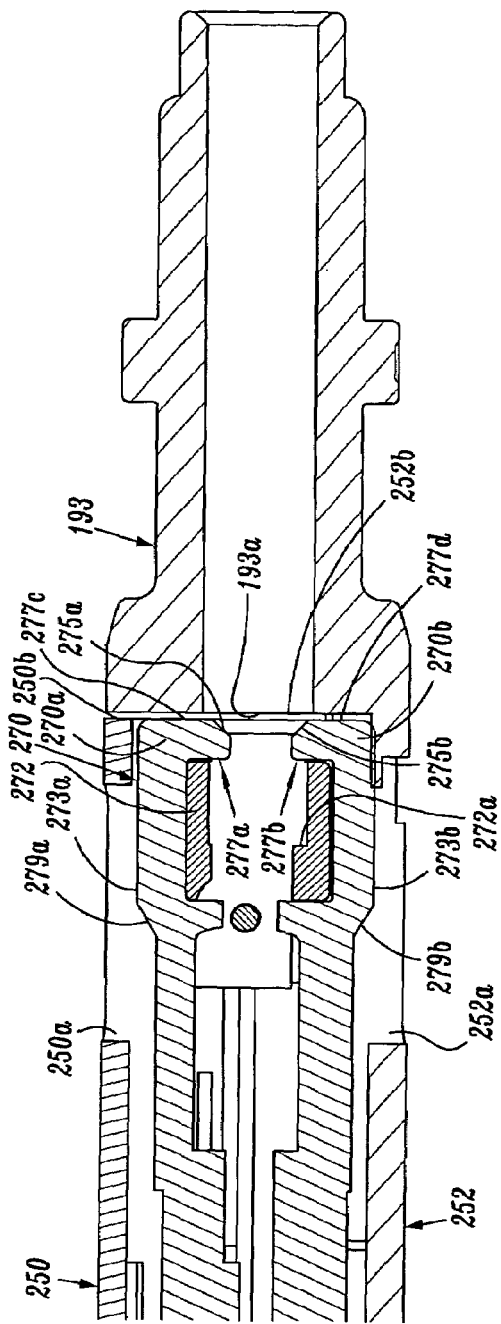
FIG. 15 is an enlarged vertical cross-sectional view of the proximal end of the DLU as would be seen along line 15—15 of FIG. 9 with the DLU assembled.

With reference to FIGS. 15–19, a method of connecting DLU 16 to the distal end of the elongate body 14 is discussed. As seen in FIG. 15, prior to insertion of insertion tip 193 into the open end of the distal end of elongate body 14 (not here shown), drive assembly 212 preferably is in the proximal-most position (e.g., such that the proximal-most facing surfaces 277c, 277d of proximal-most fingers 270a, 270b of drive assembly 212 are in close proximity to distal facing surfaces 250b, 252b of the distal ends of upper and lower housing halves 250, 252 provided near the distal facing surfaces 193a of insertion tip 193). Drive assembly 212 preferably is maintained in the proximal-most position by a normal resistive force which maintains anvil assembly 20 and cartridge assembly 18 unapproximated or open. The normal resistive force is created by a cam roller 286 of drive assembly 212 (FIG. 11) engaging a cam surface (not shown) of anvil assembly 20. For a detailed discussion of the operation of cam roller 286, reference is made to International Application Serial No. PCT/US02/32031, filed on Oct. 4, 2002, entitled "Surgical Stapling Device".

Figure 16:
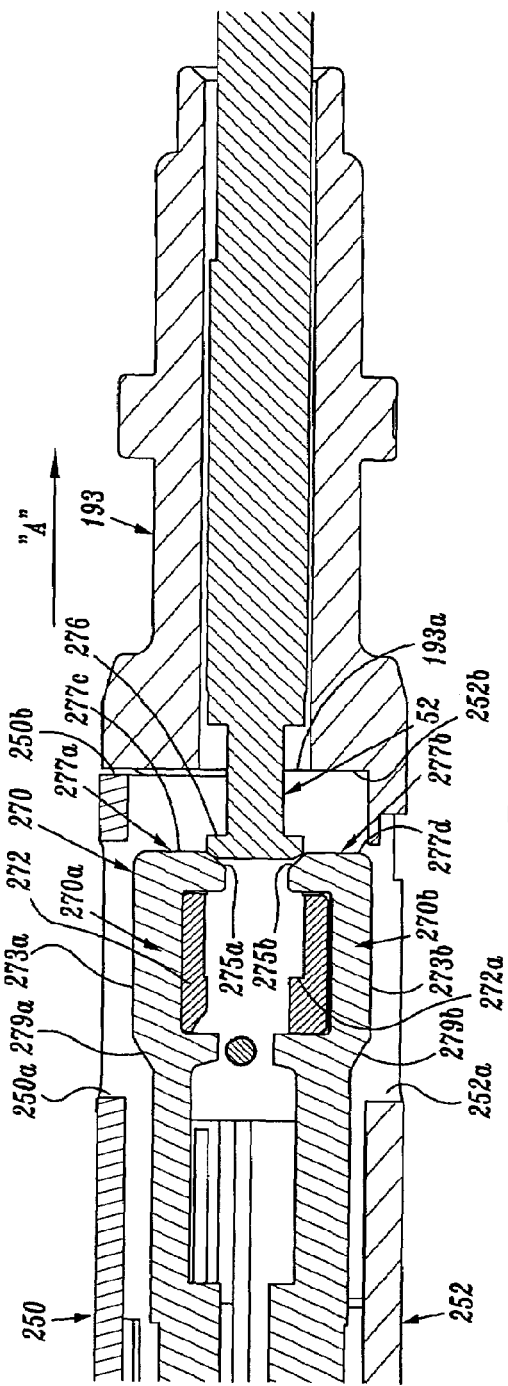
FIG. 16 is an enlarged vertical cross-sectional view of the proximal end of the DLU as would be seen along line 15—15 of FIG. 9, with the DLU assembled, illustrating a stage in the coupling of the DLU to the distal end of the drive rod of the elongate body.

As seen in FIG. 16, as insertion tip 193 is inserted into the distal end of elongate body 14 (not shown), in the direction of arrow "A", distal end 276 of control rod 52 abuts against angled surfaces 275a, 275b of fingers 270a, 270b. Initially, the closing or approximation of anvil assembly 20 and cartridge assembly 18 by distal displacement of control rod 52 (e.g., by distally advancing knobs 32 and/or a first actuation of movable handle 24) will overcome the normal resistive force and displace drive assembly 212 in a distal direction until tabs 273a, 273b of fingers 270a, 270b are below or in registration with and biased into respective elongate slots 250a, 252a of upper and lower housing halves 250 and 252.

Drive assembly 212 is maintained in axial position relative to housing 200 with tabs 273a, 273b in registration with slots 250a, 252a due to a significant resistance created by the force required to clamp and fire apparatus 10. The axial location of elongate slots 250a, 252a and of tabs 273a, 273b of drive member 212 are calculated to axially coincide based on the force required to approximate cartridge and anvil assembly 18, 20. While tabs 273a, 273b are in radial registration with slots 250a, 250b, further distal advancement of drive assembly 212 is substantially resisted by the distal force required to advance drive assembly 212 sufficiently forward through cartridge assembly 18, to clamp tissue between the cartridge and the anvil assembly 18, 20, and to fire and form the staples. A second actuation of movable handle 24 overcomes that resistance and advances drive member 272 to effect clamping and firing. As this initially occurs, fingers 270a, 270b are urged radially outward into slots 250a, 250b by distal end 276 of control rod 52.

More particularly, the initial continued displacement of control rod 52 in a direction opposite to arrow "A", relative to drive assembly 212, will result in a camming action between angled surfaces 275a, 275b of fingers 270a, 270b and distal end 276 of control rod 52 which urges and biases fingers 270a, 270b and respective tabs 273a, 273b radially outward, in the direction of arrows "B", and into elongate slots 250a, 252a formed in housing 200.

Figure 17:
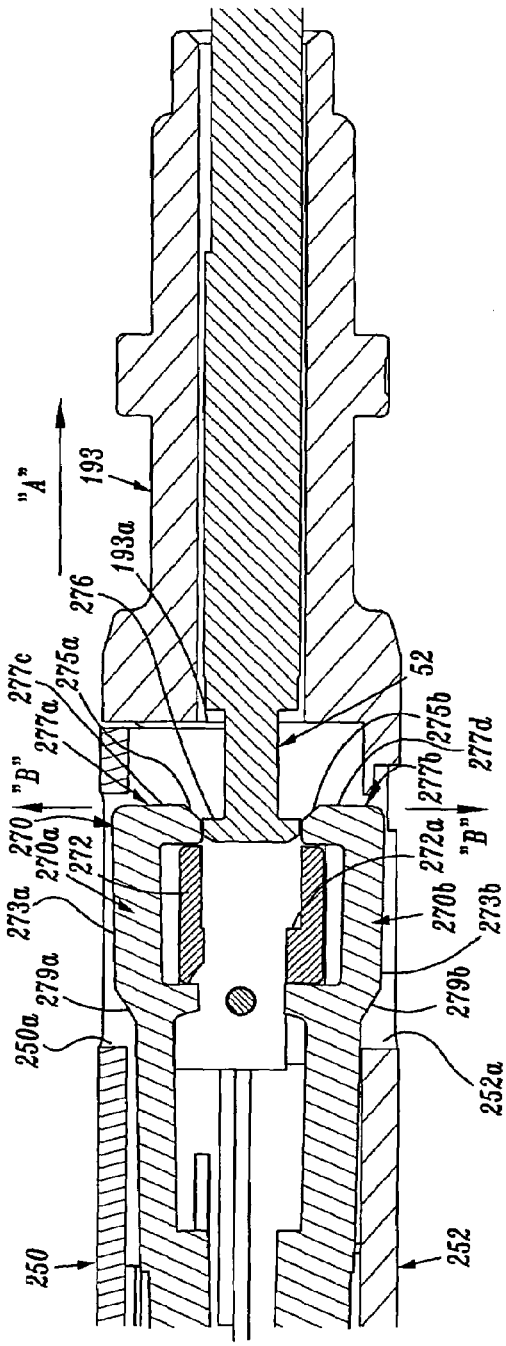
FIG. 17 is an enlarged vertical cross-sectional view of the proximal end of the DLU as would be seen along line 15—15 of FIG. 9, with the DLU assembled, illustrating another stage of the connecting of the DLU to the distal end of the drive rod of the elongate body.

Preferably, slots 250a, 252a are diametrically opposed to each other and are formed in and through upper and lower housing halves 250 and 252, respectively. When tabs 273a and 273b are positioned in slots 250a and 252a, respectively, the distal edges, here shown as angled transition surfaces 279a, 279b of tabs 273a, 273b, are adjacent the distal edges of slots 250a, 252a (as seen in FIG. 17) and thereby axially secure to temporarily prevent further distal movement of drive assembly 212 within housing portion 200 of DLU 16. While tabs 273a, 273b are forced into slots 250a, 250b of upper and lower housing halves 250, 252 (as seen in FIG. 17), head 276a or distal end 276 of control rod 52 is allowed to pass distally beyond respective in-turned tips 277a, 277b of fingers 270a, 270b.

Distal end 276 of control rod 52 has one or more engagement surfaces, preferably, and here shown as, including surfaces on head 276a (FIG. 14) which correspond to angled surfaces 275a, 275b of fingers 270a, 270b and a smaller diameter annular recess 276b (FIG. 14) just proximal of head 276a and partially defined by head 276a.

Figure 18:
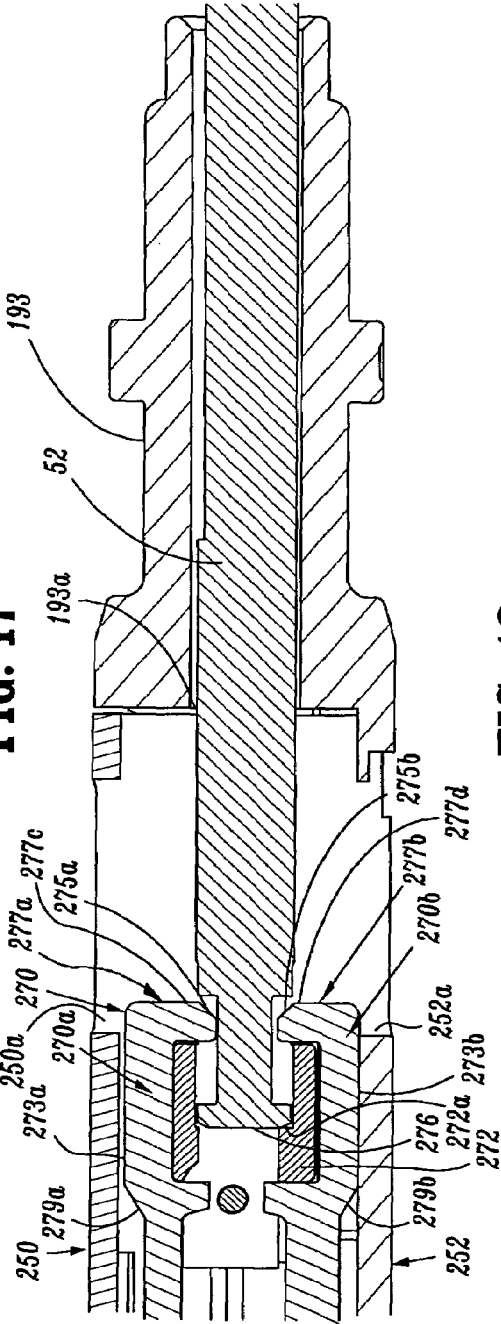
FIG. 18 is an enlarged vertical cross-sectional view of the proximal end of the DLU as would be seen along line 15—15 of FIG. 9, with the DLU assembled, illustrating yet another stage of the connecting of the DLU to the distal end of the drive rod of the elongate body.

As shown in FIG. 18, when distal end 276 of control rod 52 passes distally beyond in-turned tips 277a, 277b of fingers 270a, 270b, fingers 270a, 270b return to their un-urged or un-biased radially inward condition and snap, preferably audibly, over distal end 276, and preferably onto control rod 52, at a location within control rod recesses 276b, to properly connect or lock DLU 16 to the drive member or control rod 52 of elongate body 14 of stapling apparatus 10.

Following the aforementioned connection of engagement section 270 of drive assembly 212 to control rod 52, control rod 52 is further advanced distally within drive member 272 by the continuation of the second actuation of movable handle 24, until distal end 276 of control rod 52 contacts or otherwise operatively engages a proximal-facing surface or other internal part, here, a shoulder 272a (FIGS. 15–19) formed within drive member 272 (FIG. 18). Continued actuation of handle 24 causes the distal edges of slots 250a, 252a and the inner surface of upper and lower housing halves 250, 252 act against angled transition surfaces 279a, 279b and along the outer edge of tabs 273a, 273b to drive tabs 273a, 273b beyond slots 250 and within housing 200 to maintain fingers 270a, 270b closed onto control rod 52. As such, during the second actuation of movable handle 24, distal end 276 of control rod 52 engages shoulder 272a of drive member 272 to distally advance working head 268 of drive assembly 212 into cartridge and anvil assemblies 18, 20 to clamp tool member 17 and fire stapling apparatus 10.

Preferably, as best seen in FIGS. 15–18, each finger 270a, 270b includes an angled transition surface 279a, 279b, respectively, between the main portions of drive members 212 and tabs 273a, 273b. In this manner, if needed, as drive assembly 212 is advanced in the direction of arrow "A" to advance tabs 273a, 273b beyond elongate slots 250a, 252a, transition surfaces 279a, 279b act as camming surfaces against upper and lower housing halves 250, 252 to thereby urge fingers 270a, 270b back towards one another.

In the event that drive assembly 212 is located in a non-proximal-most position when DLU 16 is moved into the distal end of elongate body 14 for coupling one to the other, and/or in the event that drive assembly 212 is not properly connected to a drive member, e.g., control rod 52, the distal movement of control rod 52 during jaw member approximation and/or at least during clamping and firing of staples nevertheless will cause distal end 276 of control rod 52 to contact fingers 270a, 270b of drive assembly 212, as seen in FIGS. 16 and 17, and the camming action between angled surfaces 275a, 275b of fingers 270a, 270b and distal end 276 of control rod 52 will urge and bias fingers 270a, 270b and respective tabs 273a, 273b radially outward, in the direction of arrows "B", and into elongate slots 250a, 252a until distal end 276 of control rod 52 passes distally beyond respective in-turned tips 277a, 277b of fingers 270a, 270b and becomes properly engaged with and fully operatively connected to drive assembly 212.

Figure 19:
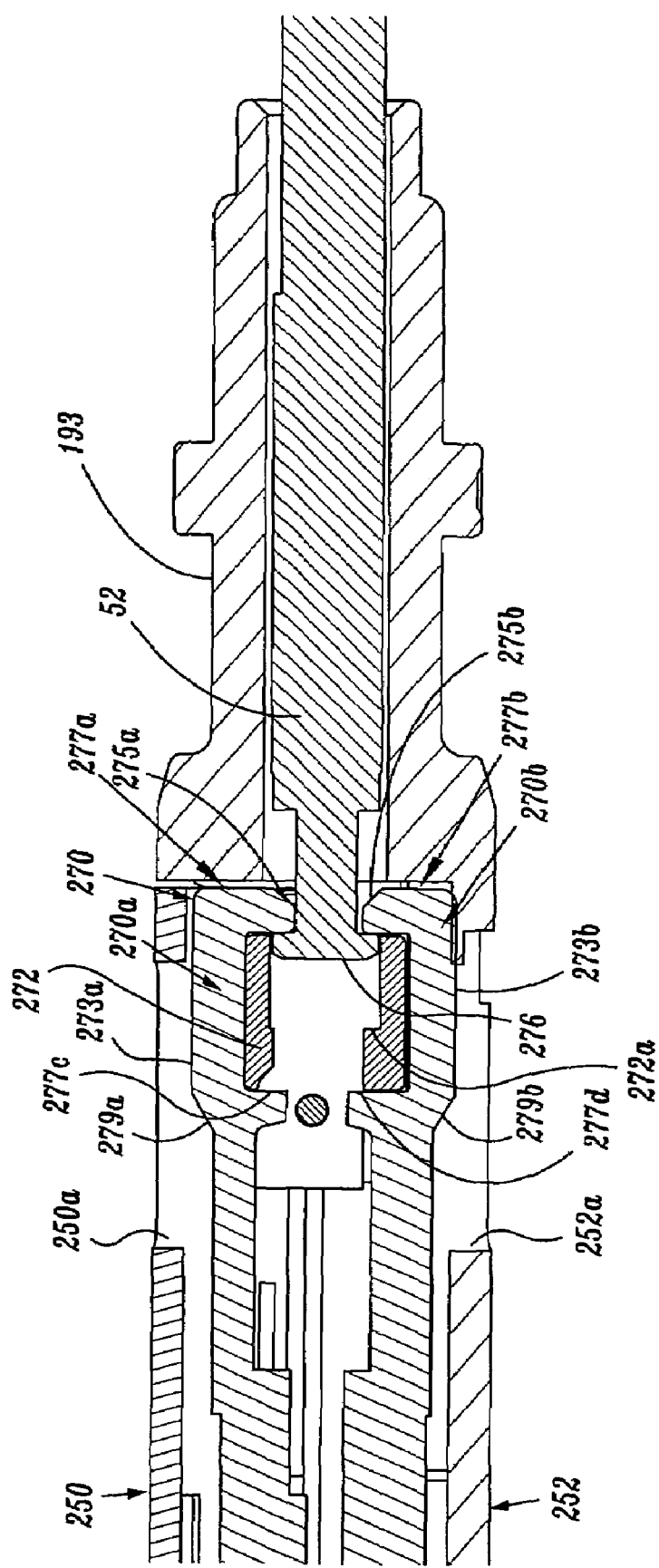
FIG. 19 is an enlarged vertical cross-sectional view of the proximal end of the DLU as would be seen along line 15—15 of FIG. 9, with the DLU assembled, illustrating still another stage of the connecting of the DLU to the distal end of the drive rod of the elongate body.
Figure 20:
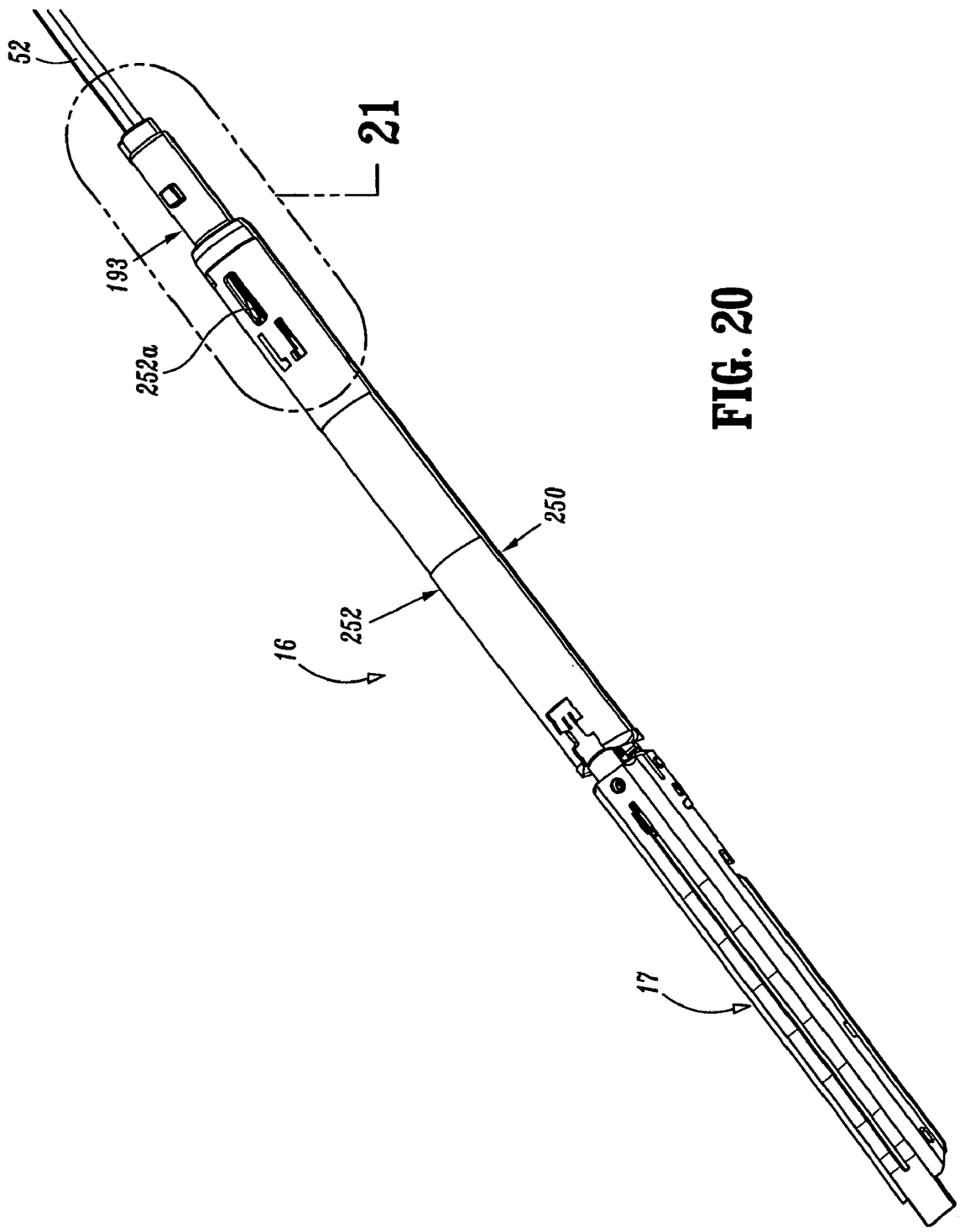
FIG. 20 is top perspective view of a DLU according to the present disclosure.
Figure 21:
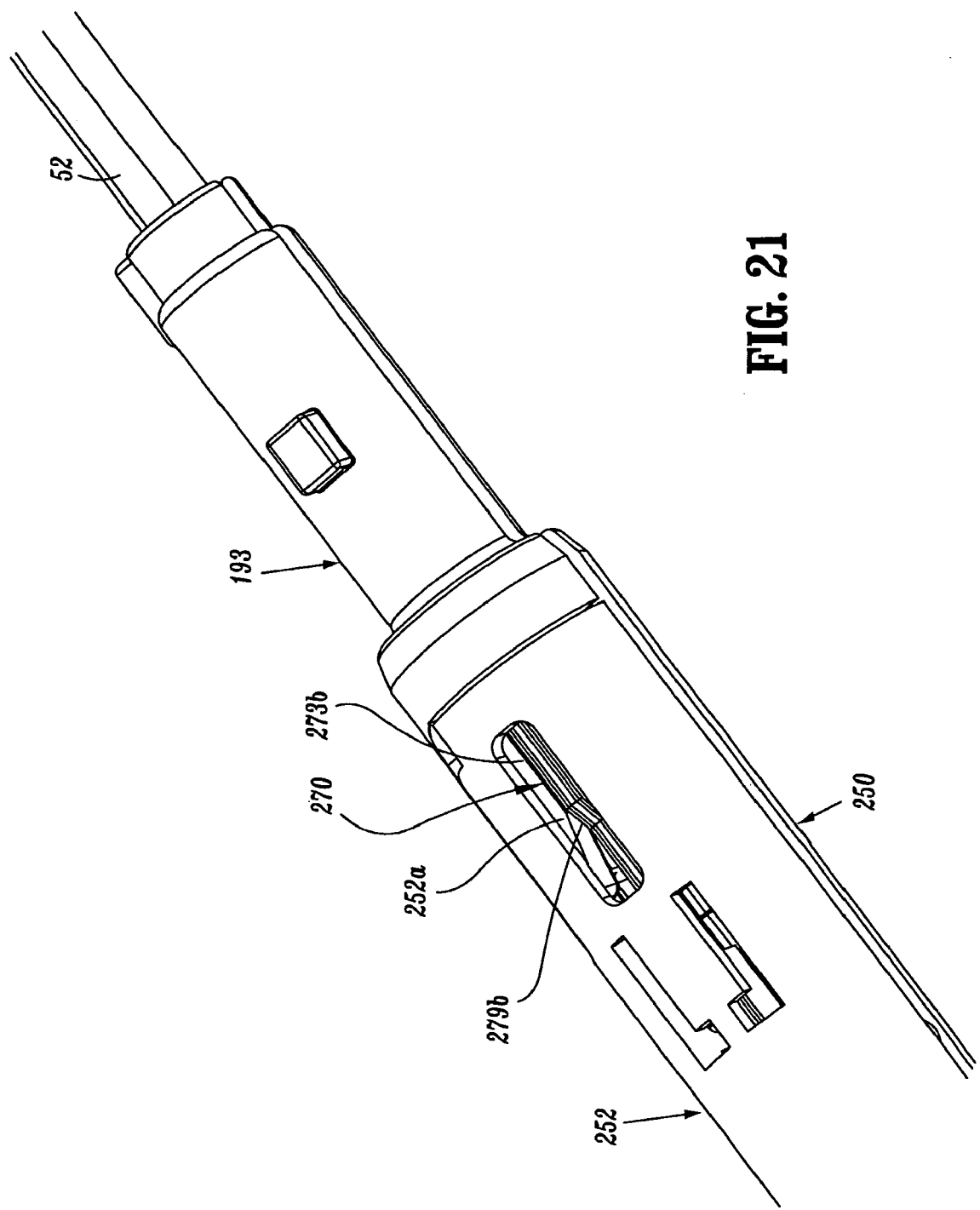
FIG. 21 is an enlarged top perspective view of the indicated area of detail of FIG. 20.
Figure 22:
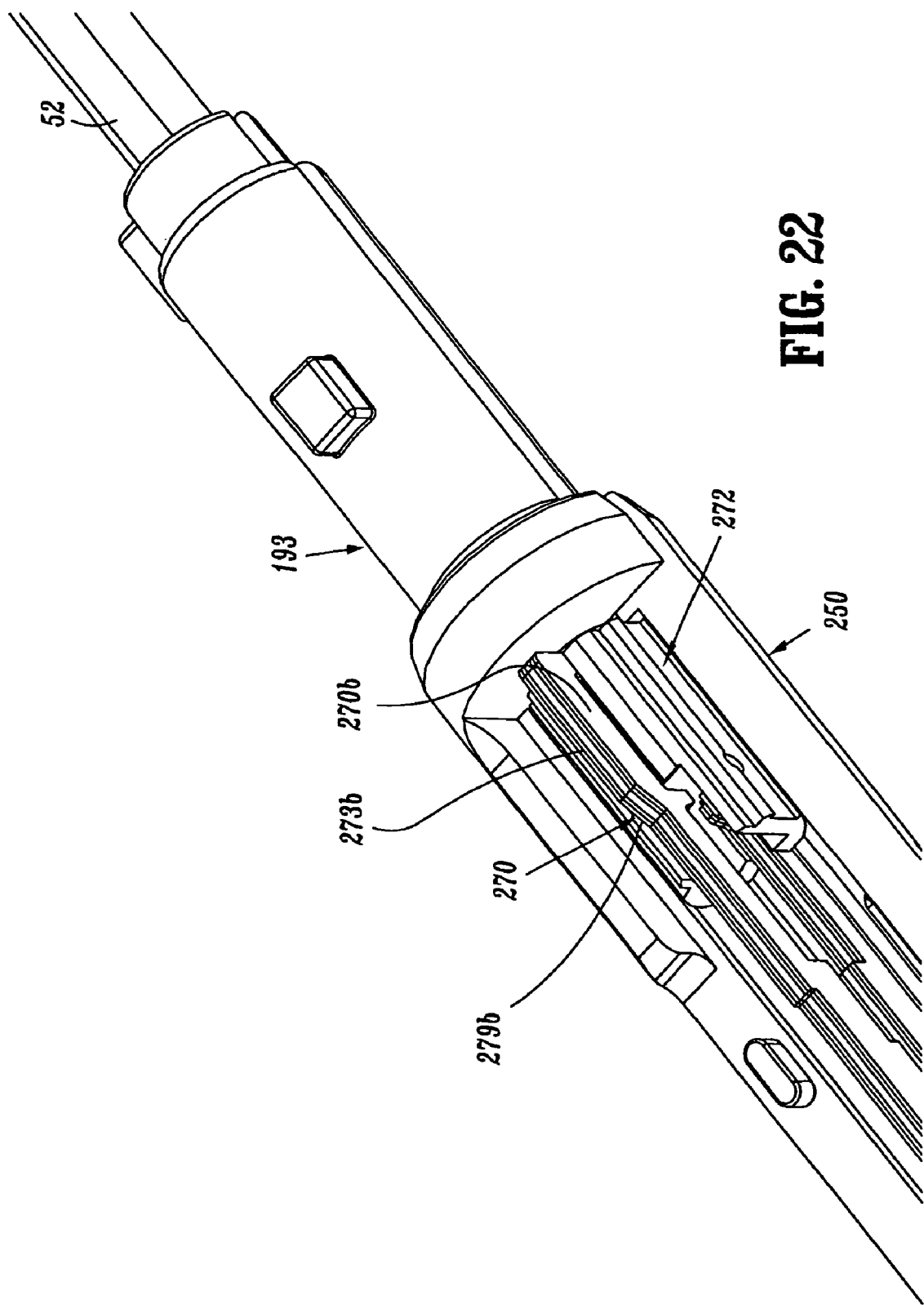
FIG. 22 is an enlarged top perspective view of the indicated area of detail of FIG. 20 with the lower housing removed.

FIG. 19 shows drive assembly 212 retracted to the proximal-most position and thereby un-clamping and/or un-approximating cartridge and anvil assemblies 18, 20.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A surgical apparatus comprising:
   a housing;
   a control rod extending distally from the housing; and
   a loading unit supportable on a distal end of the housing, the loading unit including:
      a housing portion including a pair of axially oriented opposed elongated slots formed therein said control rod being movable in an axially direction of said housing portion; and
      a drive assembly slidably supported within the housing portion of the loading unit, the drive assembly adapted to engage the control rod and including at least one resilient finger, wherein each resilient finger extends radially inwardly with respect to the housing portion, wherein when the distal end of the control rod is axially advanced in said direction to engage the at least one resilient finger, the distal end of the control rod biases the at least one resilient finger radially outward into the slots of the housing portion.

2. The surgical apparatus according to claim 1, wherein the housing portion of the loading unit includes an upper housing half portion and a lower housing half portion, and each of the upper and lower housing half portions includes one of the pair of slots formed therein.

3. The surgical apparatus according to claim 2, wherein the slots formed in each of the upper and lower housing half portions of the loading unit are radially oriented.

4. The surgical apparatus according to claim 3, wherein the slots extend at least partially into the housing portion of the loading unit.

5. The surgical apparatus according to claim 3, wherein the slots extend completely through the housing portion of the loading unit.

6. The surgical apparatus according to claim 5, wherein each resilient finger of the loading unit includes a tip and wherein the tips are oriented towards one another.

7. The surgical apparatus according to claim 6, wherein the resilient fingers of the loading unit return to an unbiased state when an enlarged distal end of the control rod has passed distally beyond the tips of the resilient fingers.

8. The surgical apparatus according to claim 7, wherein the surgical apparatus is a stapler.

9. A loading unit for use on a distal end of a surgical stapling apparatus comprising a tool assembly having a cartridge housing a plurality of staples, an anvil moveable with respect to said cartridge, and a control rod, the loading unit comprising:
   a housing portion including a pair of axially oriented opposed elongated slots formed therein, said control rod being movable in an axially direction of said housing portion; and
   a drive assembly slidably supported within the housing portion of the loading unit, the drive assembly adapted to engage the control rod of the surgical stapling apparatus to drive said staples housed in said cartridge, and including at least one resilient finger, wherein each resilient finger extends radially inwardly with respect to the housing portion, wherein when the distal end of the control rod is axially advanced in said direction to engage the at least one resilient finger, the distal end of the control rod biases the at least one resilient finger radially outward into the slots of the housing portion.

10. The loading unit according to claim 9, wherein the housing portion includes an upper housing half portion and a lower housing half portion, and each of the upper and lower housing half portions includes one of the pair of slots formed therein.

11. The loading unit according to claim 10, wherein the slots formed in each of the upper and lower housing half portions are radially oriented.

12. The loading unit according to claim 11, wherein the slots extend at least partially into the housing portion.

13. The loading unit according to claim 11, wherein the slots extend completely through the housing portion.

14. The loading unit according to claim 13, wherein each resilient finger includes a tip and wherein the tips are oriented towards one another.

15. The loading unit according to claim 14, wherein the resilient fingers return to an unbiased state when an enlarged distal end of the control rod has passed distally beyond the tips of the resilient fingers.

16. The loading unit according to claim 15, wherein the loading unit functions as a surgical stapler.

* * * * *